(12) United States Patent
Bill et al.

(10) Patent No.: US 8,057,994 B2
(45) Date of Patent: Nov. 15, 2011

(54) INVESTIGATION OF DNA SAMPLES

(75) Inventors: Martin Bill, Birmingham (GB); Ricky Paul Young, Birmingham (GB)

(73) Assignee: Forensic Science Service Ltd., London (GB)

( * ) Notice: Subject to any disclaimer, the term of this patent is extended or adjusted under 35 U.S.C. 154(b) by 237 days.

(21) Appl. No.: 11/178,045

(22) Filed: Jul. 8, 2005

(65) Prior Publication Data

US 2006/0014195 A1  Jan. 19, 2006

(30) Foreign Application Priority Data

Jul. 9, 2004  (GB) .................................. 0417763.0

(51) Int. Cl.
  C12Q 1/68     (2006.01)
  C12P 19/34    (2006.01)
  C12M 1/00     (2006.01)
  C12M 1/34     (2006.01)
  C07H 21/02    (2006.01)
  C07H 21/04    (2006.01)

(52) U.S. Cl. ..... 435/6; 435/91.2; 435/283.1; 435/287.2; 536/23.1; 536/24.3

(58) Field of Classification Search ............. 435/6, 91.2, 435/283.1, 287.2; 536/23.1, 24.3
See application file for complete search history.

(56) References Cited

U.S. PATENT DOCUMENTS

| | | | |
|---|---|---|---|
| 5,710,028 A | 1/1998 | Navot et al. | |
| 6,713,253 B1 | 3/2004 | Duff et al. | |
| 2002/0007248 A1 | 1/2002 | Gill et al. | |
| 2003/0216870 A1* | 11/2003 | Wolber et al. | 702/27 |

FOREIGN PATENT DOCUMENTS

| | | | |
|---|---|---|---|
| WO | WO 99/14368 | * | 3/1999 |
| WO | 03/083138 A | | 10/2003 |
| WO | WO 03/083138 | * | 10/2003 |

OTHER PUBLICATIONS

Ernest et al, Molecular tracking of mountain lions in the Yosemite Valley region in California: genetic analysis using microsatellites and fecal DNA, 2000, Molecular Ecology, 9, 433-441.*
Hey et al, Multilocus methods for estimating population sizes, migration rates and divergence time, with applications to the divergence of Drosophilla pseudoobsucura and D. persimilis. Genetica, 2004, 167, 747-760.*
Levinson et al, Genome scan for schizophrenia, 1998, Am J. Psycahitry, 155, 741-750.*
Duewer et al, NIST mixed stain study 3: Signal Intensity balance in commercial short tandem repeat multiplexes, 2004, Anal. Chem., 76, 6928-6934.*
Stefano et al, Ananlysis of a short tandem repeat locus on chromosome 19; 1996, Int. J. legal Med., 108, 256-258.*
Gill, P. et al. "An investigation of the rigor of interpretation rules for STRs derived from less that 100 pg of DNA," Forensic Science International, vol. 112, No. 1, Jul. 24, 2000, pp. 17-40.
Gill, P. "Role of Short Tandem Repeat DNA in forensic casework in the UK-past, present, and future perspectives," Biotechniques, vol. 32, No. 2, Feb. 2002, pp. 336-385.
Gill, P. et al. "Interpreting simple STR mixtures using allele paek areas," Forensic Science International, vol. 91, No. 1, 1998, pp. 41-53.
Bill, M. et al. "Pendulum—a guideline-based approach to the interpretation of STR mixtures," Forensic Science International, vol. 148, No. 2-3, Mar. 10, 2005, pp. 181-189.
Paranavitana, "Non-radioactive Detection of K-*ras* mutations by Nested Allele Specific PCR and Oligonucleotide Hybridization", *Molecular and Cellular Probes* 12, 309-315, 1998.
Wu, et al., "Allele-specific Enzymatic Application of β-globin Genomic DNA for Diagnosis of Sickle Cell Anemia", PNAS, vol. 88, pp. 2757-2760, 1989.
Brownie, et al., "The Elimination of Primer-Dimer Accumulation in PCR", *Nucleic Acids Research*, vol. 25, No. 16, pp. 3235-3241, 1997.
Heath, et al., "Universal Primer Quantitative Fluorescent Mutiplex (UPQFM) PCR: A Method to Detect Major and Minor Rearrangements of the Low Density Lipoprotein Receptor Gene", *Med Genet 2000*; 37:272-280, 1999.
Newton, et al., "Analysis of Any Point Mutation in DNA. The Amplification Refractory Mutation System (ARMS)", *Nucleic Acids Research*, vol. 17, No. 7, pp. 2503-2516, 1989.
Shuber, et al., "A Simplified Procedure for Developing Mutiplex PCRs", Genome Research, *Cold Spring Harbor Laboratocy Press ISSN*, 5:488-493, 1995.

(Continued)

Primary Examiner — Stephen Kapushoc
Assistant Examiner — Narayan Bhat
(74) Attorney, Agent, or Firm — Merchant & Gould P.C.

(57) ABSTRACT

A method of investigating a DNA sample is provided involving taking at least two sub-samples from the sample, amplifying the sub-samples, analyzing the sub-samples to obtain identity information and amount of that identity about one or more alleles indicated as present in the sub-samples in respect of 5 or more loci and establishing identity information deemed representative of the sample from the sub-samples, wherein identity information from a sub-sample about a particular identity is included in the identity information deemed representative of the sample when that particular identity is indicated as present by one or more of the sub-samples analyzed, the amount of that particular identity in the identity information deemed representative of the sample being a weighted combination based on the amount of that particular identity in the sub-samples. In this way useful profiles can be obtained more often than they are at present, with reduced costs and with reduced expertise and time requirements.

12 Claims, 1 Drawing Sheet

OTHER PUBLICATIONS

Old, "Detection of Mutations by the Amplification Refractory Mutation System (Arms)", Methods in Molecular Biology, US, Humanna Press, Inc., Clifton, NJ, vol. 9, pp. 77-84, 1991.

Wang et al., "Large-scale Identification, Mapping, and Genotyping of Single-nucleotide Polymorphisms in the Human Genome", Science, US, American Association for the Advancement of Science, vol. 280, pp. 1077-1082, 1998.

Hoogendoom et al., "Genotyping Single Nucleotide Polymorphisms by Primer Externsion and High Performance Liquide Chromatography" Human Genetics, Berlin, DE, vol. 104, pp. 89-93, 1999.

Curran, J.M., et al., "Interpreting DNA Mixtures in Structured Populations", Journal of Forensic Science, vol. 44, No. 5, Sep. 1999, pp. 987-995.

Weir, B.S., et al., "Interpreting DNA Mixtures", Journal of Forensic Science, vol. 42, No. 2, Mar. 1997, pp. 213-222.

Clayton, T.M., et al., "Analysis and Interpretation of Mixed Forensic Strains Using DNA STR Profiling", Forensic Science International, vol. 91, 1998, pp. 55-70.

P. Gill, et al., "Interpreting Simple Mixtures Using Allele Peak Areas", Forensic Science International, vol. 91, Jan. 9, 1998, pp. 41-53.

P. Gill, "An Assessment of the Utility of Singlenucleotide Polymorphisms (SNPs) for Forensic Purposes", International Journal of Legal Medicine, vol. 114, Apr. 2001, pp. 204-210.

Gill, P., et al., "Interpretation of simple mixtures of when artifacts such as stutters are present: With special reference to multiplex STRs used by the Forensic Science Service." Forensic Science International, vol. 95, No. 3, Aug. 12, 1998, pp. 213-224, XP001027029.

Clayton, T.M., et al., "Analysis and Interpretation of Mixed Forensic Stains Using DNA STR Profiling" Forensic Science International, Elsevier Scientific Publishers Ireland LTD, IE, vol. 91, No. 1, Jan. 9, 1998, pp. 55-70, EP001013202.

Gill, P., et al., "Development of guidelines to designate alleles using an STR multiplex system", Forensic Science International, vol. 89, No. 3, 1997, pp. 185-187.

Weir, B.S., et al., "Interpreting DNA mixtures" Journal of Forensic Sciences, vol. 42, No. 2, Mar. 1997, pp. 213-222, XP001012657.

Gill, P., et al., "Interpreting Simple STR Mixtures Using Allele Peak Areas" Forensic Science International, Elsevier Scientific Publishers Ireland LTD, IE, vol. 91, No. 1, 1998, pp. 41-53, XP001012655.

Gill, Peter, et al., "Automated short tandem repeat (STR) analysis in forensic casework: A strategy for the future", Electrophoresis, vol. 16, No. 9, 1995, pp. 1543-1552, XP001027034.

Gill et al. "An investigation of the rigor of interpretation rules for STRs derived from less than 100 pg of DNA", Forensic Science International, vol. 112, 2000, pp. 17-40.

Curran, J.M. et al. "Interpretation of repeat measurement DNA evidence allowing for multiple contributors and population substructure", Forensic Science International, vol. 148, 2005, pp. 47-53.

* cited by examiner

INVESTIGATION OF DNA SAMPLES

This invention concerns improvements in and relating to the investigation of DNA samples.

The investigation of samples to establish the profile of the DNA they contain is useful in a number of forensic science and other applications. The profile is generally formed of a series of identities of alleles present in the DNA. The results may be incomplete or of low reliability in situations where the amount of DNA in the sample is small or in other situations. Existing techniques are usually based on the investigation of a number of replicates, sub-samples, taken from the sample, with a requirement that an identity be present in each before it is accepted as part of the profile for the DNA. This and other prior art approaches restrict the occasions on which the profile can be used.

The present invention has amongst its aims to provide an approach to investigation which enables useful profiles to be obtained more often than they are at present. The present invention has amongst its aims to ensure that the profiles obtained are more reliable. The present invention has amongst its aims to reduce the cost and/or training level and/or expertise and/or time involved in investigating a DNA sample. The present invention is principally related, but not restricted, to achieving these three aims According to a first aspect of the invention we provide a method of investigating a DNA sample, the method comprising:

taking at least two sub-samples from the sample;
analysing the sub-samples to obtain identity information about one or more alleles indicated as present in the sub-samples; and
establishing identity information deemed representative of the sample from the sub-samples;

wherein identity information from a sub sample about a particular identity is included in the identity information deemed representative of the sample when that particular identity is indicated as present by one or more of the sub-samples analysed.

The identity information deemed representative of the sample may be identity information not observed in and/or not corresponding to identity information for any of the sub-samples.

The number of sub-samples the particular identity needs to be indicated as present in may be N-Y, where N is the number of sub-samples analysed and Y is at least 1 and less than N. N may be 2 and Y may be 1.

Preferably, in respect of one or more of the particular identities contributing to the identity information deemed representative of the sample, the identity information includes information on the amount of that identity detected. The amount may be expressed in terms of a peak height and/or the amount may be expressed in terms of a peak area.

Preferably the information on the amount of that identity determined for a plurality of the sub-samples is considered when establishing the amount in relation to the identity information representative of the sample. Preferably the amount from all sub-samples is considered. Preferably the amount is considered whether a positive or zero amount for that identity is indicated by a sub-sample. Preferably the amount in relation to the identity information representative of the sample represents a weighted combination of the amounts from the sub-samples.

Preferably a greater weighting is given the more of the sub-samples the particular identity is present in. Preferably a greater weighting is given the great the amount of that identity detected in the sub-samples.

Preferably the amount in relation to a particular identity in the identity information representative of the sample is based upon a square root of the amount in relation to that particular identity for one or more of the sub-samples. The amount in relation to a particular identity in the identity information representative of the sample may be equivalent to taking the average of the amounts on a logarithmic scale. Preferably the multiple of the roots of the amount for that identity for all of the sub-samples is used. The sum of the roots of the amount for that identity for all of the sub-samples may be used. The root may be the n'th square root, where n is at least 2. Preferably n is the number of sub-samples analysed. The number of sub-samples analysed may be 2, 3, 4 or greater.

The method of investigation may particularly be used to consider quantitatively small DNA samples. Small samples may be those with a DNA content of less than 250 pg or even less than 50 pg.

The method of investigation may be used to establish identity information deemed representative of a sample when the information from one or more sub-samples alone does not meet predetermined requirements.

The sub-samples taken from the sample together may form part or all of the sample. Preferably the sub-samples are taken in a manner that provides each sub-sample should be an equivalent of the others in terms of the DNA it contains. The number of sub-samples may be in the range 2 to 10.

The sub-samples may be subjected to PCR or other amplification techniques. The identities of alleles at one or more loci may be considered. STR or SNP based identities may be considered. Preferably multiple loci are considered.

The allele identity information may be obtained by an analysis instrument. The identity information may be used directly or may be provided as a data file for future use.

Preferably the method provides for generating the identity information deemed representative of the sample from the identity information from the sub-samples in a time period of less than 20 minutes per sample and ideally less than 10 minutes per sample. Preferably the method provides for generating the identity information deemed representative of the sample from the identity information from the sub-samples for in a time period of less than 2 hours for 15 samples and ideally less than 1 hour for 15 samples. The identity information deemed representative of the sample may be generated from the identity information from the sub-samples analysed in respect of 5 or more loci, more preferably 8 or more loci and ideally 10 or more loci.

BRIEF DESCRIPTION OF DRAWINGS

Various embodiments of the invention will now be described, by way of example only, and with reference to the accompanying drawings in which.

Advances in the sensitivity of methods for analysing samples containing DNA and advances in the reliability of interpretation procedures applied to the results have allowed samples containing very low levels of DNA to be successfully considered. The applicant now makes extensive use of so called "low copy number" or "LCN" analysis procedure. Details of such a procedure are to be found in PCT/GB01/

01657, the contents of which are hereby incorporated by reference, particularly in relation to the interpretation procedure and rules therefore disclosed therein.

In such existing LCN procedures, two identical sub-samples of the sample to be considered are taken and subjected to separate, but identical analysis (PCR, followed by allele determination by the inspection of peaks in the profile).

Figure 1A:
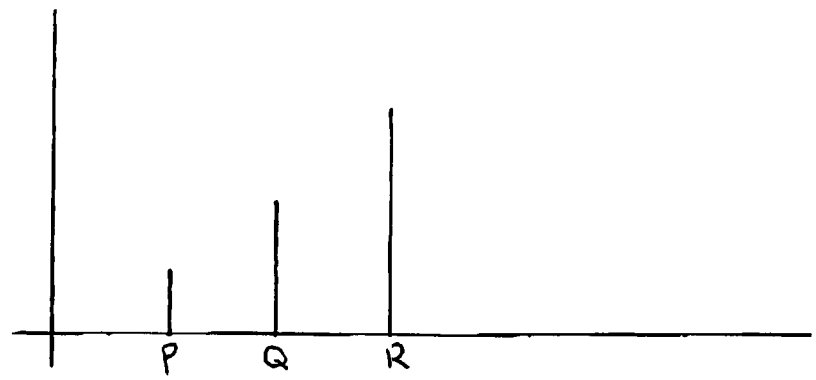
FIG. 1a illustrates the identities detected in the analysis of a first sub-sample.
Figure 1B:
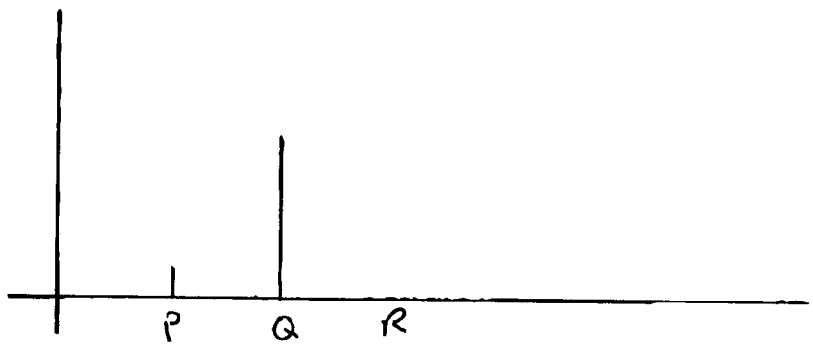
FIG. 1b illustrates the identities detected in the analysis of a second sub-sample.

Typical results from two sub-sample results are shown schematically in FIGS. 1a and 1b. These results are obtained by subjecting sub-samples of the DNA to PCR and analysis using one of a variety of techniques. The results are then visualised using one of a number of commercially available instruments such as Genotyper, Genemapper or TrueAllele. Identity, height and/or area information is usually obtained as a result. Generally this is outputted as a data file.

In FIG. 1a, three different allele identities are suggested as being present, allele identities P, Q and R. The peak height/area for the three identities is different, with R being >Q and Q being >P.

In FIG. 1b the results only show two allele identities, allele identities P and Q. There is no indication that R is present.

Under the existing procedure and rules, as peak P is present in both sub-samples, the rules for the interpretive procedure say this allele identity can be used in the consideration of the sample. However, as peak R is present in the first sub-sample, but not in the second sub-sample the rules for the existing interpretive procedure say this allele identity is not to be used in the further consideration of the sample.

Figure 2:
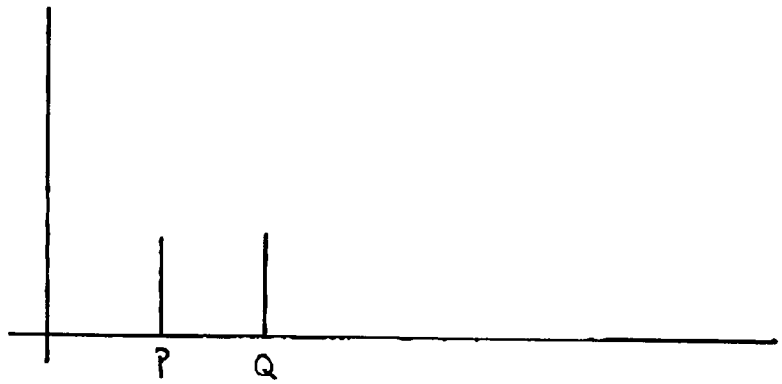
FIG. 2 illustrates the combined result calculated with respect to the old rules for considering sub-samples.

Although not generally presented in this way, the result of the consideration of the identity information from the two sub-samples, using the old approach, to give the identity information representative of the sample is that set out in FIG. 2, namely just peaks P and Q.

Where the analysis of a sample suggests allele identities in the profile for one or either sub-sample only, then the potential information on that allele does not feature in the subsequent consideration. Hence, information is potentially lost and the usefulness of the interpretation for that sample is diminished. Where a number of alleles suffer this problem then a successful consideration may not be possible at all. There are samples at present, therefore, which cannot be interpreted effectively using existing procedures and rules.

Using manual interpretation of the sub-sample results by highly trained and experienced expert it is sometimes possible to take a greater number of allele identities forward for consideration. However, such an approach is subjective, is time consuming and expensive.

The present invention provides an interpretive procedure that is based upon forming a consensus result from the individual results for the sub-samples. Thus a continuous quantitative model is used.

Figure 3:
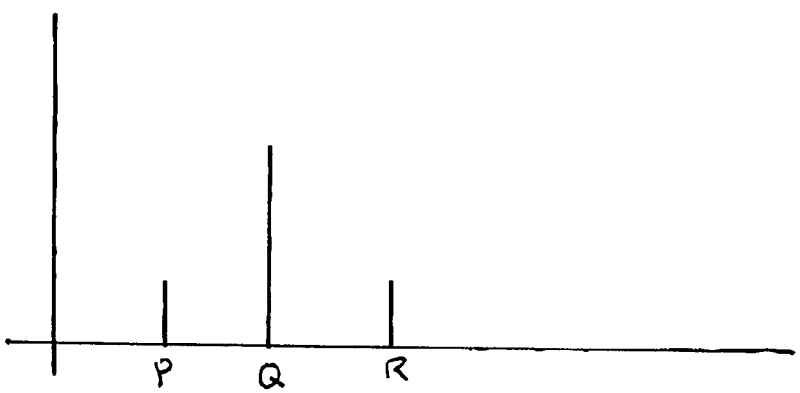
FIG. 3 illustrates the combined result calculated with respect to the present invention.

The new rule approach gives the profile/allele identities of FIG. 3 for further consideration as being the identity information representative of the sample. The manner in which the consensus is reached is as follows, with n being the number of sub-samples considered. The nth root of the peak area for each identity in each sub-sample result is taken. The nth root value for an identity from each sub-sample is added to the nth root value for that identity from other sub-samples. This is done for all identities.

Referring to the illustrated example, therefore, only 2 sub-samples are being considered and so it is the square root that is taken. FIG. 1a has peak area values of 4 for identity P, 9 for identity Q and 16 for identity R. FIG. 1b has peak area values of 1 for identity P and 9 for identity Q. As a result the consensus peak area, FIG. 3, for identity P is 2 (2×1), the consensus peak height for identity Q is 9 (3×3) and the consensus peak height for identity R is 2 (4×f, where f is a chosen weighting factor for zero indications, in this case 0.5).

In another way of approaching the generation of a consensus profile, and referring to the illustrated example, again only 2 sub-samples are being considered and so it is the square root that is taken. FIG. 1a has peak area values of 4 for identity P, 9 for identity Q and 16 for identity R. FIG. 1b has peak area values of 1 for identity P and 9 for identity Q. As a result the consensus peak area for identity P would be 3 (2+1), the consensus peak height for identity Q would be 6 (3+3) and the consensus peak height for identity R would be 4 (4+0). This consensus profile is not illustrated.

The approaches thus place greater emphasis on identities that appear in all sub-samples than those that only appear in some. Those that appear in some, but not all, get greater weight than those that appear in only one. Accounting for identities that appear in only one sub-sample result is, however, made. Whilst the use of the nth root is one manner of weighting for the consensus result, others could be used.

In the case of the illustrated example, all three identities within the consensus peak heights are then used in the further consideration. The further consideration may be provided according to one or more techniques. For instance, the consensus may be used directly as information to be loaded into a database and/or to be searched against a database for matches. It is possible to subject the consensus to further processing before the further consideration. It may be processed using one or more rule sets to determine the information from the consensus which progresses to the further consideration Not only does the present inventions procedure and rules allow consideration where it would not have previously been possible, but it also allows in to be done in an expert system or even automated manner as the interpretation of the sub-samples is made easier. Additionally, the result of the procedure and rules is a single profile, the consensus profile. This means that the subsequent consideration is made easier and more suited to performance by software. The operator also does not need the level of training and experience previously required to achieve the result.

Overall, the procedure and rules in test implementations have been able to generate results in a few minutes compared with many times under the prior art approach. Furthermore, the procedure and rules of the present invention have been able to generate useful results in twice as many of the problem DNA samples when compared with the prior art approach.

In the simplified example given above, two sub-samples are considered and an identity in any one features in the consensus result. Where a significant number of sub-samples are considered, then the approach may be that an identity features in the consensus result if it is present in N-Y of the sub-samples, where N is the total number of sub-samples considered and Y is a predetermined threshold. In the simplified case above, N is 2 and Y is 1.

Where not all identities will feature in the consensus result, for instance N is 5 and Y is 2, then first identities are considered to see whether they are present in enough of the sub-sample results. Those that do not are set aside, those that do are subjected to the processing to give their contribution to the consensus result. In the example above, the nth root was taken. Other functions could be used, however.

Once the consensus result has been reached, the consensus result may be further processed. For instance techniques to account for preferential amplification and/or stutter and/or mixture theory may be applied.

The processed consensus result can then be used directly and/or can be loaded into a database for future consideration, search against and other functions.

Whilst the procedure and rules have been described with particular reference to solving problems in the context of LCN procedures, they are applicable to other situations involving DNA analysis. There are situations, for instance, where sufficient DNA is available to avoid having to use LCN procedures, but when the results from the two sub-samples are inspected one or both does not meet the required standard (for instance for loading on to a database). The procedure and rules of the present invention enable a consensus to be established and potentially used instead.

The invention claimed is:

1. A method of investigating a single DNA sample to provide consensus identity information deemed representative of the sample, the method comprising:
    a) taking at least two sub-samples of DNA from the sample;
    b) amplifying the sub-samples;
    c) analysing the sub-samples to obtain identity information, the identity information including an identity and an amount of that identity detected, the identity being the identity of the one or more alleles indicated as present in the sub-samples by the analysing, the analysing being applied in respect of 5 or more loci; and
    d) establishing identity information deemed representative of the sample from the sub-samples by;
        1) including, by an automated step, in the identity information deemed representative of the sample, identity information from a sub-sample about a particular identity when that particular identity is indicated as present by one or more of the sub-samples analyzed; and
        2) including, by an automated step, in the identity information deemed representative of the sample, a weighted combination for that particular identity, the weighted combination being weighted according to the amounts of that particular identity in all the sub-samples;
    thereby establishing the identity information deemed representative of the sample from the sub-samples in the form of a consensus of the identity information of the sub-samples, thereby providing the consensus identity information deemed representative of the sample;
    wherein the consensus identity information includes an identity and an amount of that identity for each identity indicated by the analysing as present in the sub-samples in respect of the 5 or more loci.

2. A method according to claim 1 in which the number of sub-samples the particular identity needs to be indicated as present in is N-Y, where N is the number of sub-samples analysed and Y is at least 1 and less than N.

3. A method according to claim 1 in which information on an amount of an identity of one or more alleles is determined and, in respect of one or more of the particular identities contributing to the identity information deemed representative of the sample, the identity information includes information on the amount of one or more alleles detected, the amount being quantified in terms of peak height or the amount being quantified in terms of peak area.

4. A method according to claim 1 in which information on an amount of an identity of one or more alleles is determined for each of the plurality of the sub-samples and the information on the amount of an identity for one or more alleles determined for each of the plurality of the sub-samples is considered when establishing the amount of that identity in relation to the identity information representative of the sample.

5. A method according to claim 4 in which the amount in relation to the identity information representative of the sample represents a weighted combination of the amounts from the sub-samples.

6. A method according to claim 5 in which a greater weighting is given the more of the sub-samples the particular identity is present in.

7. A method according to claim 5 in which a greater weighting is given the greater the amount of that identity detected in the sub-samples.

8. A method according to claim 1 in which information on an amount of an identity of one or more alleles is determined and the amount in relation to a particular allele in the identity information representative of the sample is based upon multiplying the amount of the particular allele determined by $\sqrt{n}$, for one or more of the sub-samples, where n is the number of sub-samples analysed.

9. A method according to claim 8 in which the amount in relation to a particular allele in the identity information representative of the sample for that identity for all of the sub-samples are multiplied together.

10. A method according to claim 8 in which the amount in relation to a particular allele in the identity information representative of the sample for that identity for all of the sub-samples are added together.

11. A method according to claim 1 in which information on an amount of an identity of one or more alleles is determined and the amount in relation to a particular allele in the identity information representative of the sample is equivalent to taking the average of the amounts on a logarithmic scale.

12. A method according to claim 1 in which the identity information deemed representative of the sample is generated from the identity information from the sub-samples analysed in respect of 8 or more loci.

* * * * *